US012274660B2

(12) United States Patent
Freno

(10) Patent No.: US 12,274,660 B2
(45) Date of Patent: Apr. 15, 2025

(54) SYSTEM AND METHOD FOR PROMOTING HEALING WITH TOPICAL APPLICATION OF VIBRATION

(71) Applicant: Mathew Cole Freno, Cedar Rapids, IA (US)

(72) Inventor: Mathew Cole Freno, Cedar Rapids, IA (US)

( * ) Notice: Subject to any disclaimer, the term of this patent is extended or adjusted under 35 U.S.C. 154(b) by 640 days.

(21) Appl. No.: 17/512,013

(22) Filed: Oct. 27, 2021

(65) Prior Publication Data

US 2022/0125671 A1    Apr. 28, 2022

Related U.S. Application Data

(60) Provisional application No. 63/204,801, filed on Oct. 27, 2020.

(51) Int. Cl.
*A61H 23/02* (2006.01)
*B06B 1/02* (2006.01)

(52) U.S. Cl.
CPC .............. *A61H 23/02* (2013.01); *B06B 1/02* (2013.01); *A61H 2201/165* (2013.01)

(58) Field of Classification Search
CPC .............. A61H 23/02; A61H 2201/165; A61H 2201/5025; B06B 1/02; A61F 13/02; A61F 2013/00655; A61F 2013/00697
See application file for complete search history.

(56) References Cited

U.S. PATENT DOCUMENTS

| | | | | |
|---|---|---|---|---|
| 2006/0258962 A1* | 11/2006 | Kopanic | ............ | A61H 23/0263 601/57 |
| 2006/0258963 A1* | 11/2006 | Kopanic, Jr. | ........ | A61K 9/7023 601/57 |
| 2009/0259168 A1* | 10/2009 | Prizant | ............... | A61H 23/0263 604/22 |
| 2014/0228721 A1* | 8/2014 | Ehrenreich | ........ | A61H 23/0245 601/47 |
| 2014/0243589 A1* | 8/2014 | Rowan | .................... | A61H 23/02 600/38 |
| 2017/0326024 A1* | 11/2017 | Hernandez | ............. | A61B 5/442 |
| 2019/0110949 A1* | 4/2019 | Bhatti | ..................... | A61H 23/02 |
| 2021/0259914 A1* | 8/2021 | Holbert | ............... | A61F 13/0233 |
| 2021/0393478 A1* | 12/2021 | Bhatti | ................ | A61H 23/0263 |
| 2022/0105359 A1* | 4/2022 | Rappaport | ............ | A61F 13/124 |

* cited by examiner

*Primary Examiner* — Tu A Vo
*Assistant Examiner* — Kelsey E Baller
(74) *Attorney, Agent, or Firm* — Simmons Perrine Moyer Bergman PLC

(57) ABSTRACT

A vibration appliance and method for providing vibration to a portion of an animal, the method including providing a pair of CR2450 batteries on opposite ends of a hot glue formed collection of switch, a vibrator motor, and connections therebetween, where one connection is a movable magnet which can be used to selectively connect batteries at opposite ends of the vibration appliance by manually moving a wire coupled at one end to the magnet and at another end to a switch between couplings with different batteries so that during storage the device has a long battery shelf life as no batteries are coupled at both terminals to electronic components.

10 Claims, 7 Drawing Sheets

SYSTEM AND METHOD FOR PROMOTING HEALING WITH TOPICAL APPLICATION OF VIBRATION

CROSS REFERENCE TO RELATED APPLICATIONS

The present application claims the benefit of the filing date of provisional patent application having Ser. No. 63/204,801 filed on Oct. 27, 2020, by MATHEW COLE FRENO, which application is incorporated herein in its entirety by this reference.

FIELD OF THE INVENTION

The present invention generally relates to promotion of healing by exposing a portion of a living animal to vibration, and more particularly relates to methods and system for facilitation of the application of vibration therapy to body portions in need of healing.

BACKGROUND OF THE INVENTION

In the past, the topical application of vibration to a location on a body has been done for the desired results of promoting healing in many areas including: increasing bone density and muscle mass, improving blood circulation, reducing joint pain, and countless ailments and conditions.

Vibration appliances which require power cords are well known. Similarly, handheld battery operated vibration appliances have been used widely for years.

These devices are not suitable for inclusion in a first aid kit because of the size and/or need for remote power sources.

Consequently, there exists a need for improved methods and systems for efficiently promoting healing with topical application of vibration, which are sized and configured for extended shelf life while stored in a first aid kit.

SUMMARY OF THE INVENTION

It is an object of the present invention to promote healing with the topical application of vibration.

It is a feature of the present invention to provide a vibrator coupled to an adhesive bandage.

It is an advantage of the present invention to allow for quick application of topical vibration to parts of the body which are capable of receiving an adhesive bandage.

The present invention is carried out in a "wire-less" manner, in a sense that there are no power wires extending away from a site on a body with an adhesive bandage having a vibration appliance thereon.

Accordingly, the present invention is a method of promoting healing with the topical application of vibration, comprising the steps of:
a) providing a first aid kit; with a commercial off-the shelf adhesive bandage therein;
b) providing a battery operated vibration appliance in said first aid kit;
wherein said battery operated vibration appliance includes therein:
  i) a micro on/off switch; and
  ii) a combination of two CR2450 batteries collectively having four terminals, in a parallel orientation, where a first pair of the four terminals of said combination are electrically coupled to another electronic component, in said vibration appliance;
  wherein while said vibration appliance is stored in said first aid kit, a manipulation of the micro on/off switch will not result in operation of a vibration motor, until a magnet is placed on one terminal of another pair of terminals of said four terminals;
c) placing a magnet on said one terminal of another pair of terminals and thereby making an electronic connection between said one terminal to said micro on/off switch; and
d) using said vibration appliance to provide vibration to a portion of an animal.

Additionally, the present invention is an improved system for providing vibration to a portion of an animal, the system comprising:
a micro on/off switch; and
a combination of two CR2450 batteries collectively having four terminals, in a parallel orientation, where a first pair of the four terminals of said combination are electrically coupled to another electronic component, in said vibration appliance, wherein, while said vibration appliance is stored in said first aid kit, a manipulation of the micro on/off switch will not result in operation of a vibration motor, until a magnet is placed on one terminal of another pair of terminals of said four terminals.

BRIEF DESCRIPTION OF THE DRAWINGS

The invention may be more fully understood by reading the following description of the preferred embodiments of the invention, in conjunction with the appended drawings wherein.

DETAILED DESCRIPTION

Although described with particular reference to adhesive bandages, the systems and methods of the present invention can be implemented in many different types of devices for supporting a topical vibrator, such as elastic wrapped bandages, compression sleeves, etc.

In an embodiment, the system and method of the present invention described herein can be viewed as examples of many potential variations of the present invention which are protected hereunder. The following details are intended to aid in the understanding of the invention whose scope is defined in the claims appended hereto.

Figure 1:
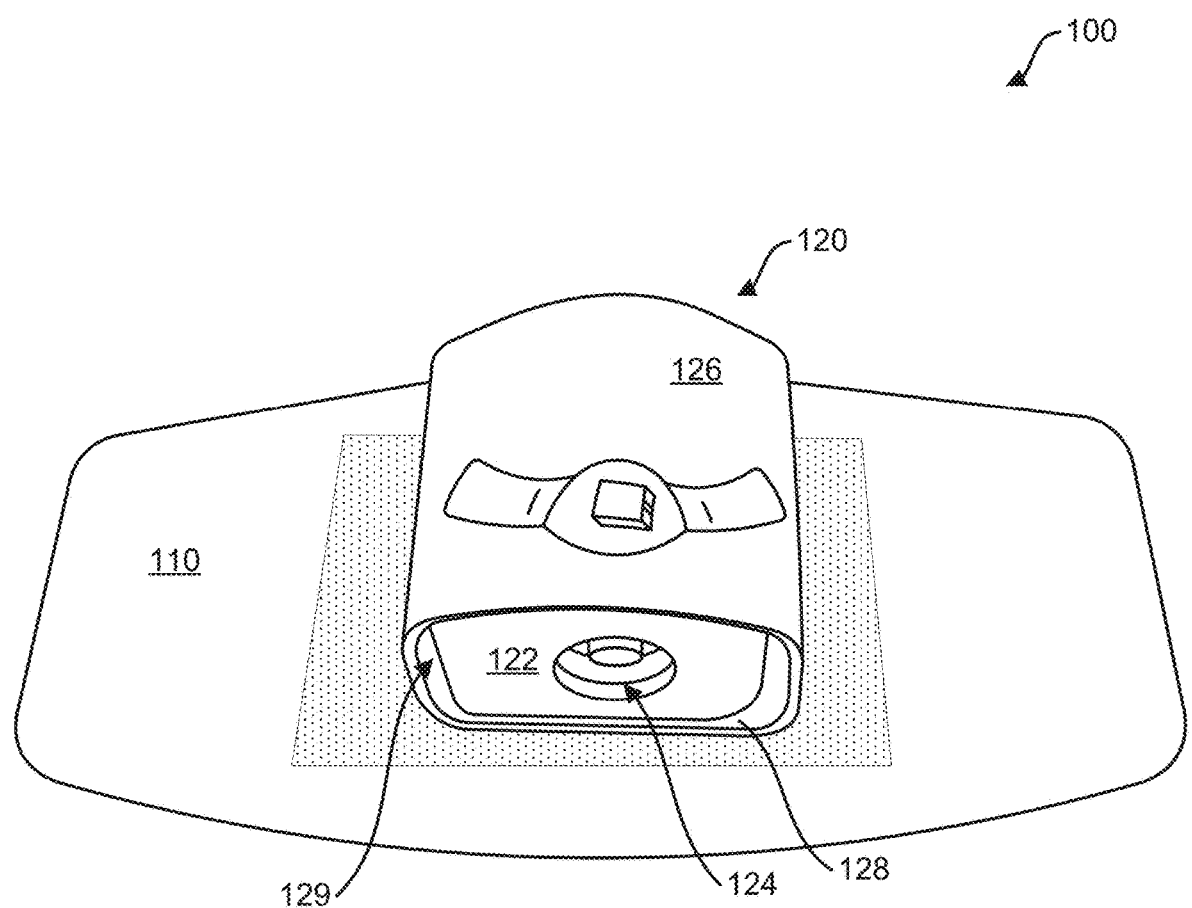
FIG. 1 is a perspective view of the adhesive bandage with topical vibration appliance, of the present invention, in a fully assembled configuration.

Now referring to the drawings wherein like numerals refer to like matter throughout, and more particularly in FIG. 1, there is shown a perspective view of the adhesive bandage with vibration capability 100, of the present invention, with an adhesive bandage 110, which could be any type of adhesive bandage or other device for coupling the vibration appliance 120 to a portion of an animal. Vibration appliance 120 is shown disposed on an outer surface of adhesive bandage 110. Innovative vibration appliance 120 has a molded glue face 122 with a micro on/off switch actuator button 124 in an orifice therethrough. Also shown is bottom side 128 and lanyard receiving side 129.

Figure 2:
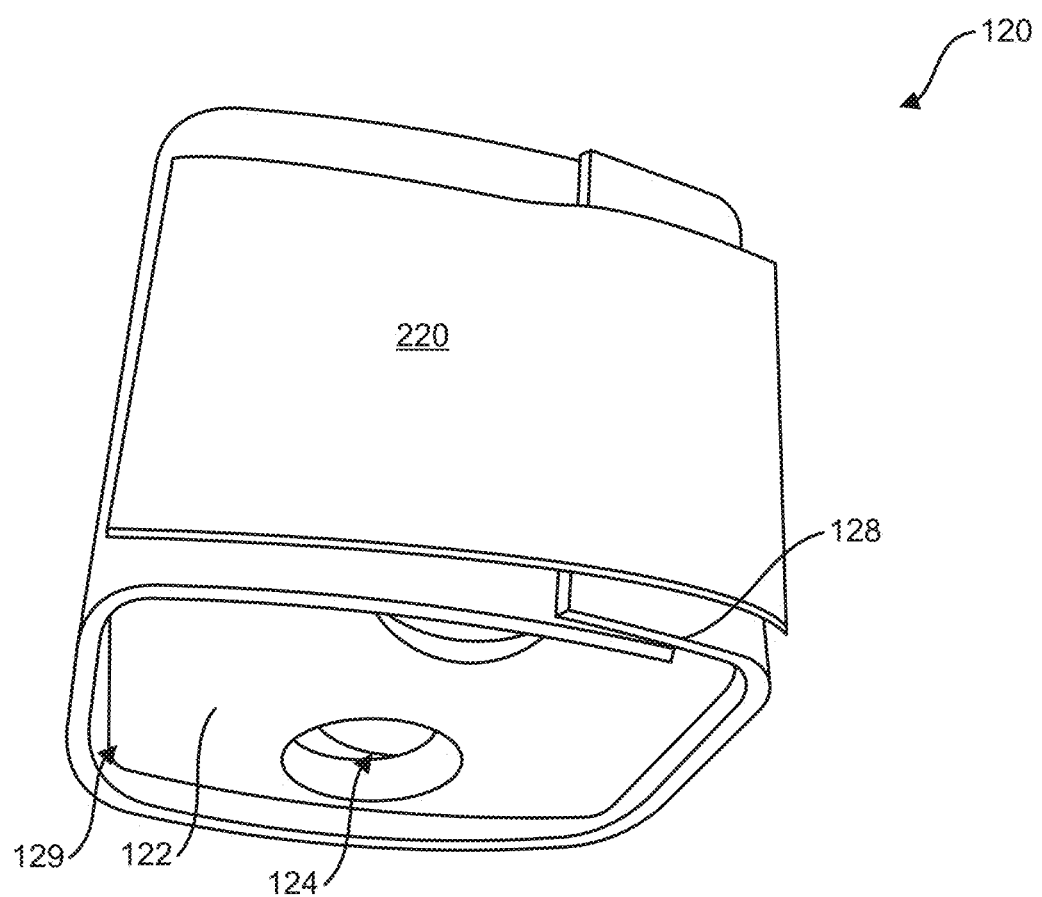
FIG. 2 is perspective view of a bottom side of the vibration appliance of the present invention.

Now referring to FIG. 2, there is shown the vibration appliance 120 after having been separated from the adhesive bandage 110 and flip over so its bottom side 128 is now upward and exposing the double-sided adhesive tape 220 on the bottom side 128 which is used to hold vibration appliance 120 to the exterior of adhesive bandage 110 when bottom side 128 is placed adjacent thereto.

Figure 3:
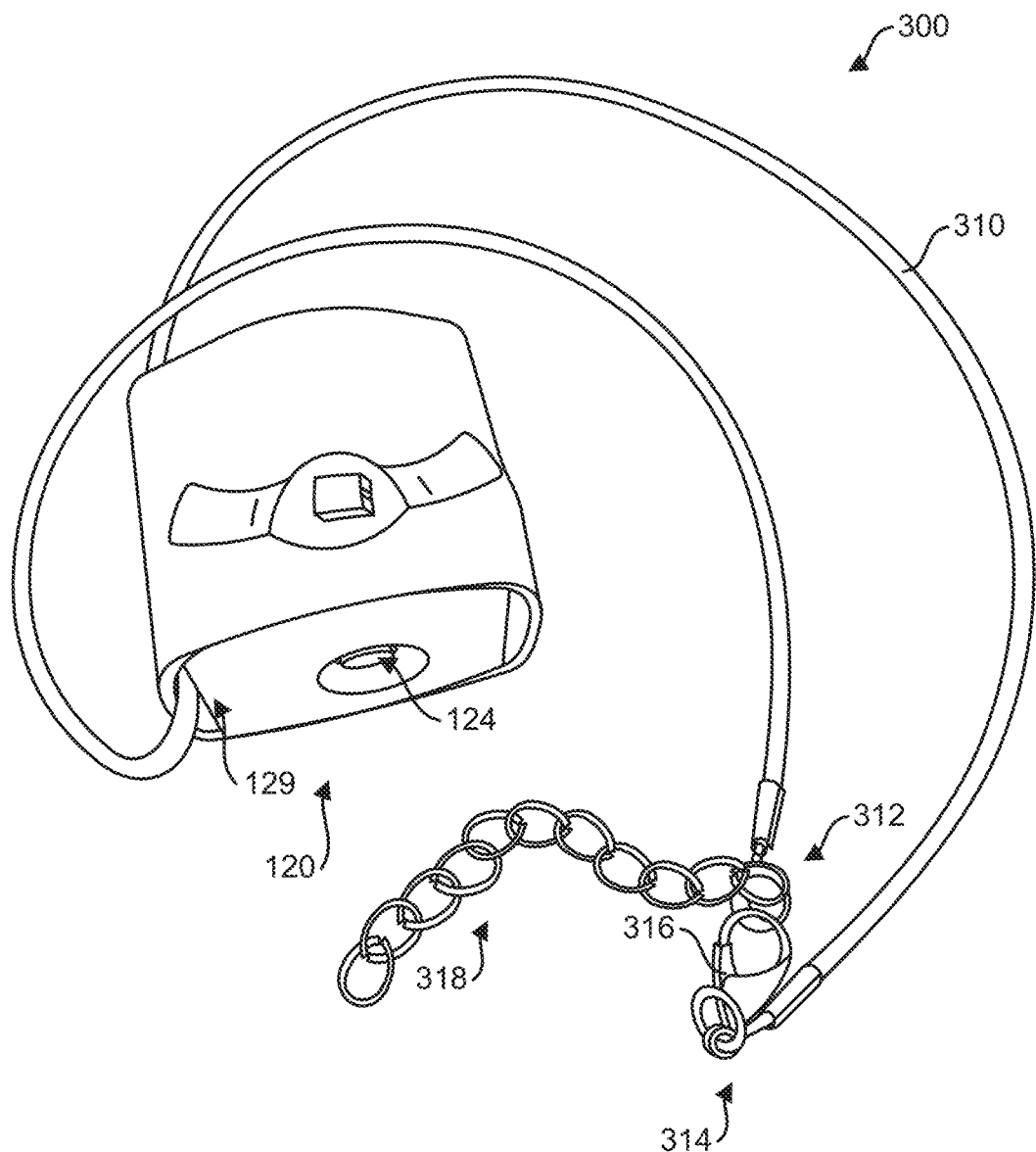
FIG. 3 is perspective view an alternate embodiment of the present invention including the vibration appliance of FIGS. 1 and 2, with an addition of a lanyard.

Now referring to FIG. 3, there is shown the vibration appliance with lanyard strap combination 300 which includes lanyard strap 310 extending through the silicone sleeve 126 at lanyard receiving side 129. Lanyard strap 310 forms a loop when lanyard end eye 312 and fixed clasp end 314 are connected together by lanyard latch gate 316. Also shown is lanyard length adjustment chain 318, which can permit the lanyard latch gate 316 to decouple from lanyard end eye 312 and to couple thereto at any intermediate links therein to allow for length adjustment of the lanyard strap 310.

Figure 4:
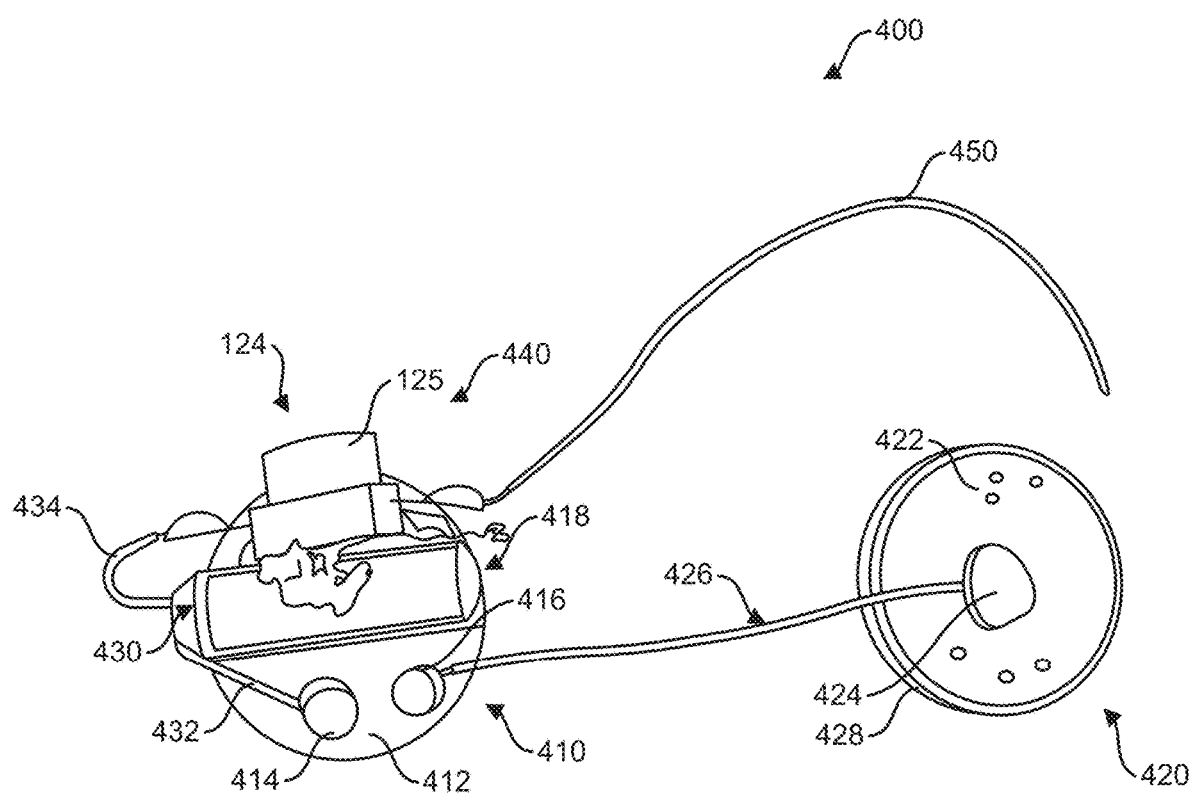
FIG. 4 is a perspective view of a portion of the electronic and other components of the present invention.

Now referring to FIG. 4, there is shown an electronic component assembly portion 400 having a first 3 V button battery 410 and a second 3 V button battery 420 with a battery to battery connecting wire 426 therebetween.

Hot glued to first 3 V button battery 410 is vibration motor 430 and micro on/off switch 440. Vibration motor to first battery wire 432 is coupled to first 3 V button battery positive terminal 412 via solder joint 414. Battery to battery connecting wire 426 is coupled to first 3 V button battery positive terminal 412 via connecting joint 416. Disposed on the opposite side from first 3 V button battery positive terminal 412 is first 3 V button battery negative terminal side 418. In this FIG. 4, the Vibration motor 430 and the micro on/off switch 440 are glued to each other and to the first battery positive terminal 412. Vibration motor 430 is coupled to micro on/off switch 440 via vibration motor to switch output wire 434.

Micro on/off switch input wire 450 is shown coupled to micro on/off switch 440 on one end and having nothing at its other end. Battery to battery connecting wire 426 is coupled to second 3 V button battery negative terminal 422 via solder joint 424. Opposite second 3 V button battery negative terminal 422 is second 3 V button battery positive terminal side 428.

The following electronic components are all available for purchase from Amazon: first and second 3 V button battery 410 and 420 are CR2450 batteries manufactured by LiCB and have model number LWUS-2450-10. The vibration motor 430 is 7 mm×25 mm is manufactured by BestTong and has model number A00000269. The micro on/off switch 440 is manufactured by MXuteuk and has model 1208.

Figure 5:
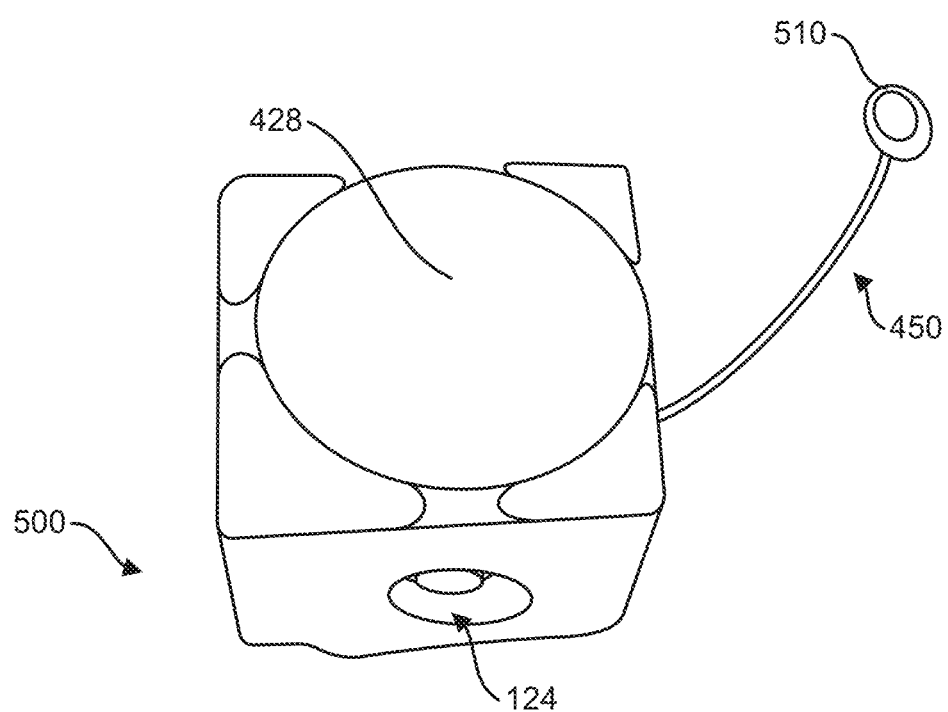
FIG. 5 is a perspective view of a portion of the invention where an adhesive has been molded around portions of the electronic components of FIG. 4.
Figure 6:
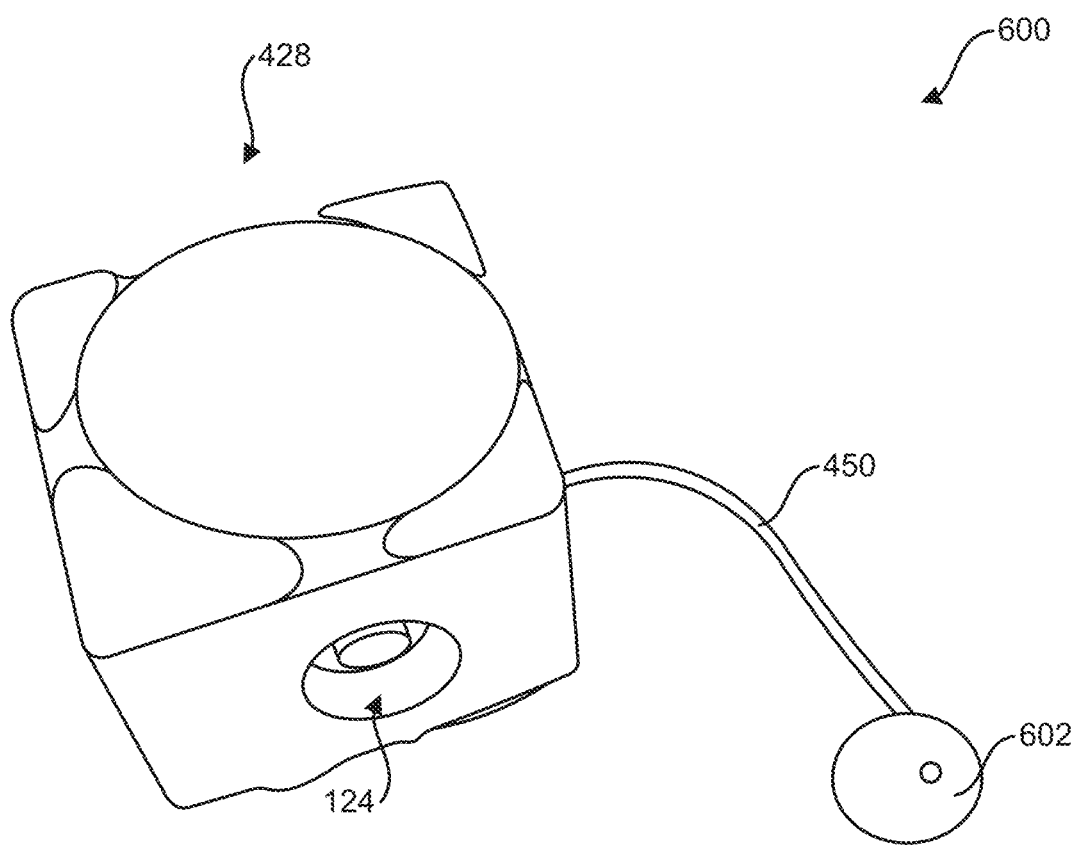
FIG. 6 is a perspective view of the components of FIG. 5 with an additional quantity of glue disposed on a portion of FIG. 5 not covered by glue.

Now referring to FIG. 5, there is shown the result of taking the assembly of FIG. 4 and placing all but the micro on/off switch input wire 450 and the second 3 V button battery 420 and portions of battery to battery connecting wire 426 in a mold with the first 3 V button battery negative terminal side 418 on an exterior side of the mold as well as glue blocking sleeve 125 with micro on/off switch actuator button 124 therein. Then hot glue is poured into the mold covering up the first battery positive terminal 412, the vibration motor 430 and the micro on/off switch 440, and the connections therebetween. Then, after the glue covers everything but the micro on/off switch input wire 450 and the battery to battery connecting wire 426, the second 3 V button battery 420 is placed inside the mold with the second 3 V button battery positive terminal side 428 facing upward. There should be enough hot glue under the second 3 V button battery 420 so that when it is pressed into the glue, glue flows up and around the sides of the second 3 V button battery 420. When the glue cools, the molded glue and vibration appliance portion assembly 500 is extracted from the mold.

To transform molded glue and vibration appliance portion assembly 500 to vibration appliance electronics and molded glue combination 600, there is simply a quantity of hot glue added to the circuit breaker circle magnet 510 to make the circuit breaker circle magnet glue handle 602.

Figure 7:
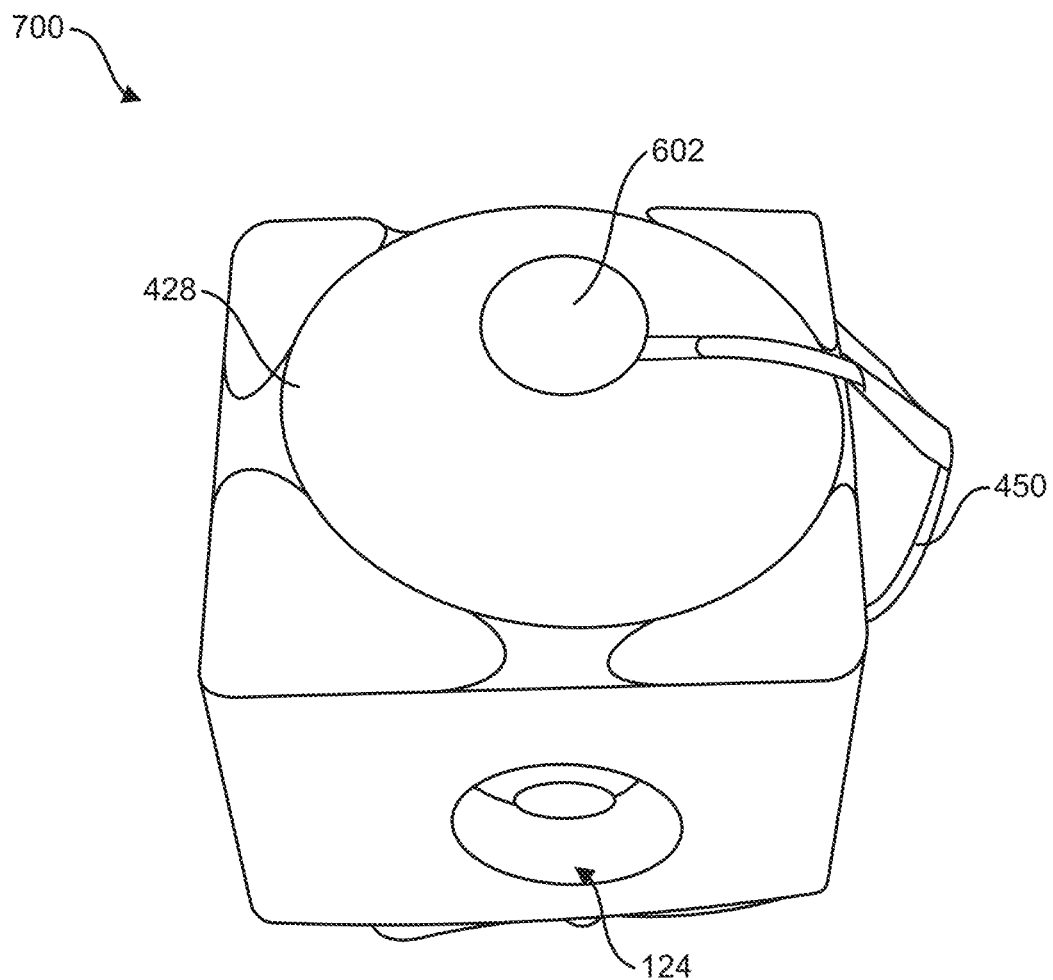
FIG. 7 is a perspective view of the present invention with the circuit breaker deployed for operation.

Now referring to FIG. 7, there is shown second 3 V button battery positive terminal side 428 exposed and on the top thereof is circuit breaker circle magnet glue handle 602 and the circuit breaker circle magnet 510 which makes the electrical connection from second 3 V button battery positive terminal side 428 to micro on/off switch 440 via micro on/off switch input wire 450.

When this battery runs out, the circuit breaker circle magnet glue handle 602 can be grasped and the circuit breaker circle magnet 510 removed from second 3 V button battery positive terminal side 428 and placed on the first 3 V button battery negative terminal side 418 (not shown but on the opposite side from second 3 V button battery positive terminal side 428).

The silicone sleeve 126 can be placed around the assembly 700, including over the circuit breaker circle magnet glue handle 602 to help hold it in contact with the second 3 V button battery positive terminal side 428.

The precise implementation of the present invention will vary depending upon the particular application.

It is thought that the method and apparatus of the present invention will be understood from the foregoing description and that it will be apparent that various changes may be made in the form, construct steps and arrangement of the parts and steps thereof without departing from the spirit and scope of the invention or sacrificing all of their material advantages. The form herein described is merely a preferred and/or exemplary embodiment thereof.

I claim:

1. A method of promoting healing with a topical application of vibration, comprising the steps of:
    a) providing a first aid kit; with a commercial off-the shelf adhesive bandage therein;
    b) providing a battery operated vibration appliance in said first aid kit;
    wherein said battery operated vibration appliance includes therein:
        i) a micro on/off switch; and
        ii) a combination of two CR2450 batteries collectively having four terminals, in a parallel orientation, where a first pair of the four terminals of said combination of two CR2450 batteries are electrically coupled to an electronic component, in said vibration appliance;
    wherein while said vibration appliance is stored in said first aid kit, a manipulation of the micro on/off switch will not result in operation of a vibration motor, until a magnet is placed on one terminal of another pair of terminals of said four terminals;
    c) placing the magnet on said one terminal of another pair of terminals of said four terminals and thereby making an electronic connection between said one terminal of another pair of terminals of said four terminals to said micro on/off switch; and d) using said vibration appliance to provide vibration to a portion of an animal.

2. The method of claim 1 wherein said step of placing the magnet further involves moving a circuit breaker circle magnet with a micro on/off switch input wire coupled thereto so that direct current at said one terminal of another pair of terminals of said four terminals is able to flow through said micro on/off switch input wire.

3. The method of claim 2 further comprising the steps of: coupling said vibration appliance to the adhesive bandage.

4. The method of claim 3 further comprising the steps of coupling a lanyard to a mass so as to inhibit separation of said vibration appliance from said mass by a distance further than a dimension of said lanyard.

5. The method of claim 1 wherein a run-time of said vibration appliance is extended by relocating said magnet to another one of said another pair of terminals.

6. The method of claim 5 wherein said step of relocating involves moving the magnet to an opposite side of said vibration appliance.

7. A system for providing vibration to a portion of an animal, the system comprising:

a micro on/off switch; and a combination of two CR2450 batteries collectively having four terminals, in a parallel orientation, where a first pair of the four terminals of said combination are electrically coupled to an electronic component, in a vibration appliance, wherein, while said vibration appliance is stored in a first aid kit, a manipulation of the micro on/off switch will not result in operation of a vibration motor, until a magnet is placed on one terminal of another pair of terminals of said four terminals.

8. The system of claim 7 further comprising a quantity of molded glue disposed about each of said micro on/off switch and said combination.

9. The system of claim 8 wherein said parallel orientation is a geometric parallel orientation between said two CR2450 batteries.

10. The system of claim 8 further comprising a micro on/off switch input wire which is coupled to said magnet.

* * * * *